United States Patent
Reider

(10) Patent No.: US 10,646,711 B2
(45) Date of Patent: *May 12, 2020

(54) INTERACTIVE MUSCLE TRAINING SYSTEM AND METHOD

(71) Applicant: Brent C. Reider, Oxford, OH (US)

(72) Inventor: Brent C. Reider, Oxford, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/391,933

(22) Filed: Apr. 23, 2019

(65) Prior Publication Data

US 2019/0247651 A1 Aug. 15, 2019

Related U.S. Application Data

(63) Continuation-in-part of application No. 15/010,372, filed on Jan. 29, 2016, now Pat. No. 10,307,589.

(51) Int. Cl.
| | |
|---|---|
| *A61N 1/36* | (2006.01) |
| *A61B 5/11* | (2006.01) |
| *A61B 5/00* | (2006.01) |
| *A61B 5/0488* | (2006.01) |

(52) U.S. Cl.
CPC ........ *A61N 1/36007* (2013.01); *A61B 5/1107* (2013.01); *A61N 1/3603* (2017.08); *A61N 1/36003* (2013.01); *A61N 1/36031* (2017.08); *A61B 5/04882* (2013.01); *A61B 5/486* (2013.01)

(58) Field of Classification Search
CPC .............. A61N 1/36007; A61N 1/3603; A61N 1/36003; A61B 5/1107; A61B 5/04882
See application file for complete search history.

(56) References Cited

U.S. PATENT DOCUMENTS

| | | |
|---|---|---|
| 5,041,974 A | 8/1991 | Walker et al. |
| 5,800,501 A | 9/1998 | Sherlock |
| D652,526 S | 1/2012 | Peddicord |
| D669,592 S | 10/2012 | Peddicord |
| D670,398 S | 11/2012 | Peddicord |
| D670,399 S | 11/2012 | Peddicord |
| D674,503 S | 1/2013 | Peddicord |
| 8,369,953 B2 | 2/2013 | Peddicord |

(Continued)

OTHER PUBLICATIONS

Laborie Medical Technologies, Pelvic Floor Therapy—Biofeedback and More: Conservative Treatment for Pelvic Floor Disorders, retrieved from website Dec. 9, 2015, www.laborie.com.

(Continued)

*Primary Examiner* — George R Evanisko
(74) *Attorney, Agent, or Firm* — Standley Law Group LLP; Jeffrey S. Standley; Adam J. Smith

(57) ABSTRACT

A system for educating a given muscle group of a user is provided. A muscle stimulation portion is configured to provide electrical stimulation which causes the muscle group to contract. A biofeedback portion is configured to monitor for muscular contractions of the muscle group. The muscle stimulation and biofeedback portions are provided on a common probe but are electrically separated from one another. The biofeedback and muscle stimulation portions provide signals to an electronic display to generate a first visualization representing the desired outcome of the provided stimulation when the muscle stimulation portion is active and a second visualization representing the muscular contractions detected when the biofeedback portion is active.

12 Claims, 13 Drawing Sheets

(56) References Cited

U.S. PATENT DOCUMENTS

| | | | |
|---|---|---|---|
| 8,784,345 B2 | 7/2014 | Peddicord | |
| 8,818,582 B2 | 8/2014 | Peddicord | |
| D716,463 S | 10/2014 | Peddicord | |
| RE45,585 E | 6/2015 | Peddicord | |
| D739,545 S | 9/2015 | Peddicord | |
| 9,173,806 B1 | 11/2015 | Dematio et al. | |
| D754,870 S | 4/2016 | Peddicord | |
| 9,372,533 B1 | 6/2016 | Agrama | |
| RE46,163 E | 9/2016 | Peddicord | |
| 9,655,808 B2 | 5/2017 | Peddicord | |
| 10,307,589 B2 * | 6/2019 | Reider | A61N 1/36007 |
| 2010/0304864 A1 | 12/2010 | Johnson et al. | |
| 2013/0066400 A1 | 3/2013 | Perryman et al. | |
| 2013/0337975 A1 | 12/2013 | Yanev et al. | |
| 2014/0057232 A1 | 2/2014 | Wetmore et al. | |
| 2014/0200432 A1 | 7/2014 | Banerji et al. | |
| 2014/0249602 A1 | 9/2014 | Colborn | |
| 2017/0252264 A1 | 9/2017 | Peddicord | |

OTHER PUBLICATIONS

InControl Medical LLC, APEX—OTC Device for Treatment of Stress Continence, retrieved from website visited Mar. 27, 2019, https://www.incontrolmedical.com/products/apex/.

InControl Medical, LLC, ATTAIN—The Ultimate Solution to Bladder and Bowel Leakage, retrieved from website visited Mar. 27, 2019, https://www.incontrolmedical.com/attain/.

Elvie, Elvie Trainer, retrieved from website visited Mar. 29, 2019, https://www.elvie.com/shop/elvie-trainer.

InControl Medical, LLC, Intensity, OTC device for Female Sexual Health, retrieved from website visited Mar. 27, 2019, https://www.incontrolmedical.com/products/intensity/.

* cited by examiner

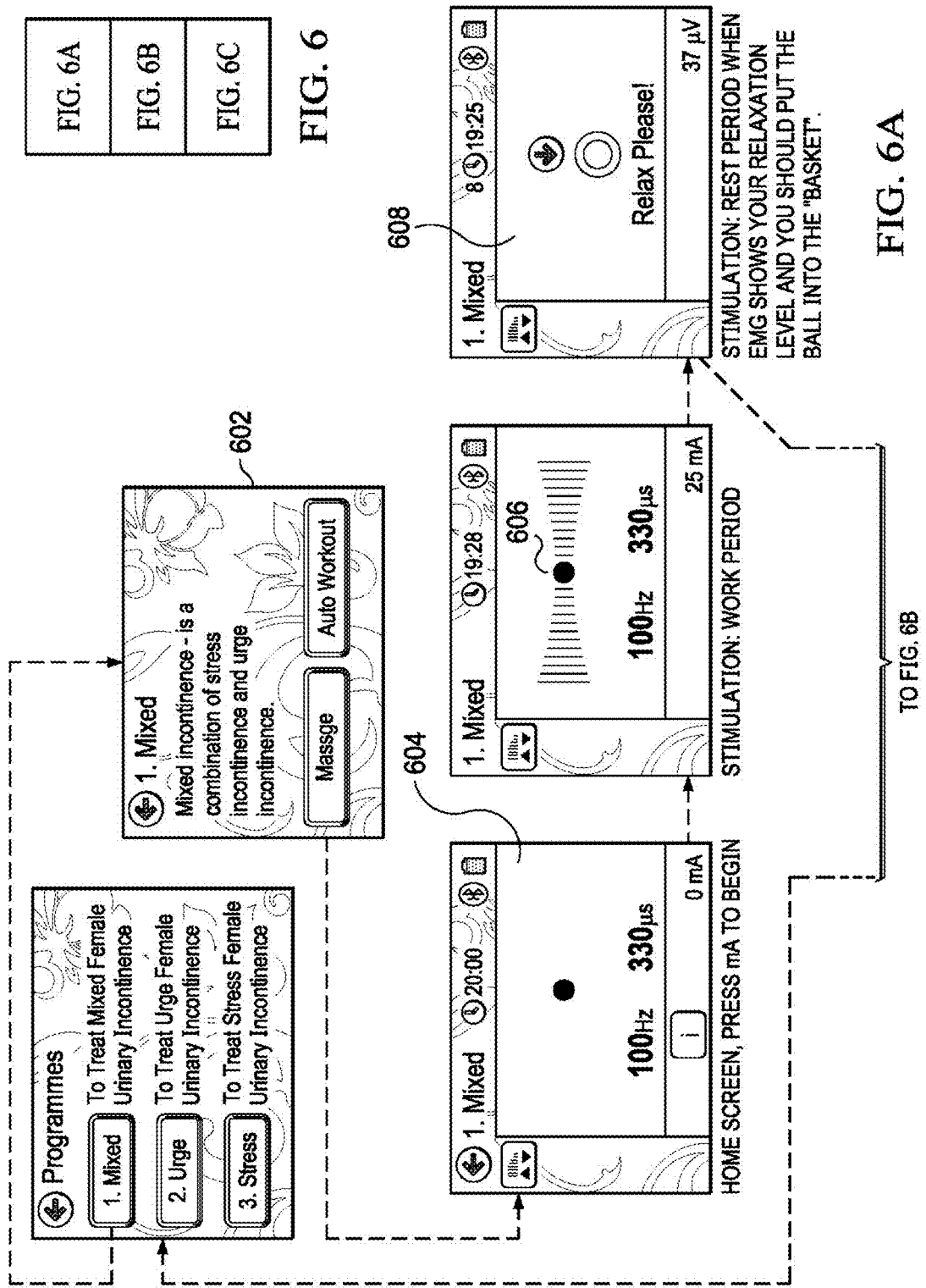

INTERACTIVE MUSCLE TRAINING SYSTEM AND METHOD

CROSS-REFERENCE TO RELATED APPLICATIONS

This application is a continuation-in-part of U.S. Non-Provisional application Ser. No. 15/010,372 filed Jan. 29, 2016, the disclosures of which are hereby incorporated by reference as if fully restated herein.

TECHNICAL FIELD

Exemplary embodiments of the present invention relate generally to systems and methods for conditioning and training the muscle response of certain muscles in humans.

BACKGROUND AND SUMMARY OF THE INVENTION

In human females, the pelvic floor muscles may become weak or lose conditioning as the result of age, childbirth, injury or disease. As a result, those with weak or unconditioned muscles may experience difficulty controlling or stopping the flow of urine. As a result, these individuals may experience episodes of incontinence, sexual dysfunction, or other undesirable situations related to muscle control. In order to improve the condition of the pelvic floor muscles and thus reduce the incidences of incontinence, improve sexual function, and/or improve other undesirable situations, individuals may perform various exercises including an exercise that involves the voluntary contraction of the pelvic floor muscles. The most well-known of these is the Kegel exercise. When performing Kegel exercises, a subject generally will attempt to contract their muscles for a short period of time, release the contraction of those muscles and then repeat this process. The desired result is the improvement of muscle tone in the pelvic floor muscles. Some individuals may have difficulty identifying the correct muscles to contract or may not hold the contraction long enough to be beneficial. In other cases, the individual may not remember to perform the exercises or lose interest and either stop performing the exercise or not perform them frequently enough to obtain a desired benefit.

There have been devices disclosed that assist a user in their efforts to learn to contract the muscles of the pelvic floor using various methods of electrically stimulating those muscles. In fact, various classes of muscle stimulators have been defined by the U.S. Food and Drug Administration including muscle stimulators for the improvement of muscle tone, muscle stimulators for the treatment of incontinence and stimulation for the treatment of muscle pain. Devices for facilitating some of these treatments are also known in the art. For example, U.S. Pat. No. 5,800,501 (Sherlock) discloses a device for providing an electrode for electrical stimulation. This same device may also be used to receive biofeedback signals. With such a device, a user may receive stimulation in order to strengthen the muscles of the pelvic floor. In addition to the stimulation portions, Sherlock also discloses a biofeedback portion. The biofeedback portion may be used to measure a user's muscle activity in response to such stimulation or as the result of exercises initiated by the user. Such a device may be of value to a user who desires to strengthen their pelvic floor muscles by combining stimulation with self-initiated muscle exercise. A user of such a device must be diligent with regard to their self-initiated exercises in order to see optimum results with regard to muscle strengthening. The use of games or similar methods of engaging a user may be beneficial in that such methods may encourage the user to persist in their exercise program. Various classes of muscle stimulators have been defined by the U.S. Food and Drug Administration including muscle stimulators for the improvement of muscle tone, muscle stimulators for the treatment of incontinence and stimulation for the treatment of muscle pain feedback.

Applications for regulated stimulation and interactive feedback extend beyond the pelvic floor muscles and incontinence issues. Various other muscle groups may be educated and re-educated to perform in desirable ways. Herein, the terms education and re-education may be used interchangeably. Examples of such applications include, but are not limited to, replantation patients, stroke victims, paralysis victims, and individuals experiencing other injuries or conditions. In such cases, the amount of muscle stimulation required for safe and optimal muscle education must be determined and utilized. In many cases, the optimal amount of muscle stimulation is specific to the particular user based on the user's physical characteristics, injury or condition, and progress within the muscle education program. Therefore, what is needed is a system and method which provides regulated muscle stimulation and interactive feedback for muscle education.

A system and method which provides regulated muscle stimulation and interactive feedback for muscle education is disclosed. The muscle education may involve neurological (hypothalamic) and spinal locomotor pattern generation. In an embodiment of such a device and system, a muscle stimulation system may be combined with a biofeedback receiving system that interacts with a plurality of games. A user of such a device may engage the muscle stimulation system to both provide conditioning to pelvic floor muscles and also to learn what sort of muscle response produces the desired conditioning of the pelvic floor muscles. A user may also use the plurality of games to encourage the user to perform exercises to strengthen the pelvic floor muscles. Games may have the benefit of encouraging the user to initiate the desired exercise and also to provide guidance to the user in regards to an optimum exercise level and technique. In an embodiment of the invention, a firewall may be created between the stimulation portion and the feedback portion to prevent the use of the feedback portion to control the stimulation. Such a firewall may be physical in nature, in other words, a physical isolation between the electronic components comprising the stimulation and biofeedback portion of an embodiment of the invention. In other embodiments of the invention, the firewall may be formed by the software programming of the embodiment. In such an example, the software may be designed to prevent interaction between the biofeedback and stimulation portions of the embodiment. In an embodiment of the device in which the firewall is formed in software, an enabling code may be implemented such that persons seeking to change or modify the device programming may be prevented from doing so without having the proper enabling code. Such an enabling code feature may also be used to prevent software modifications or game designs that may be harmful to a user of the device.

The muscle stimulation provided may be regulated to reflect a desired outcome. Too much muscle stimulation can be counter-productive as it may result in regression of muscle education. Too little muscle stimulation may not be sufficient to educate the muscles.

For each individual user the maximum therapeutic efficacy may be achieved by way of an algorithmic demonstration of sufficient muscle performance and respiration. Salient to the multi-variable algorithm is the status of the targeted muscle tissues including, but not limited to, muscle responsiveness to following the requisite task and a determination of blood flow. So, if the muscle is unable to perform specific template driven low level contraction challenges and/or exhibits any indications of spasm as monitored by EMG then the next stimulation (NMES) cycle is blocked and remains arrested for as long as the muscle or muscle group cannot perform the threshold point prequalification parameters. As such, the stimulation to be provided may be determined based on characteristics of the specific individual user.

Alternatively, or in addition, the stimulation to be provided may be determined based on the user's condition or injury. In exemplary embodiments, a visualization tool may be provided with the regulated stimulation. The visualization tool may provide a visualization of the desired outcome during periods of regulated stimulation to incorporate the user's locomotor pattern generation in therapy so as to include but not limited to procedural memory when the pattern of the objects drives action and when that perception is integral to action in the act of mapping the patterns of the world onto the patterns of the body. Alternatively, or in addition, the visualization tool may provide a visualization of the biofeedback received at the device for enhanced precision in developing specific procedural memory tasks for the specific individual user.

Further features and advantages of the devices and systems disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 6A are additional exemplary user interfaces;

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
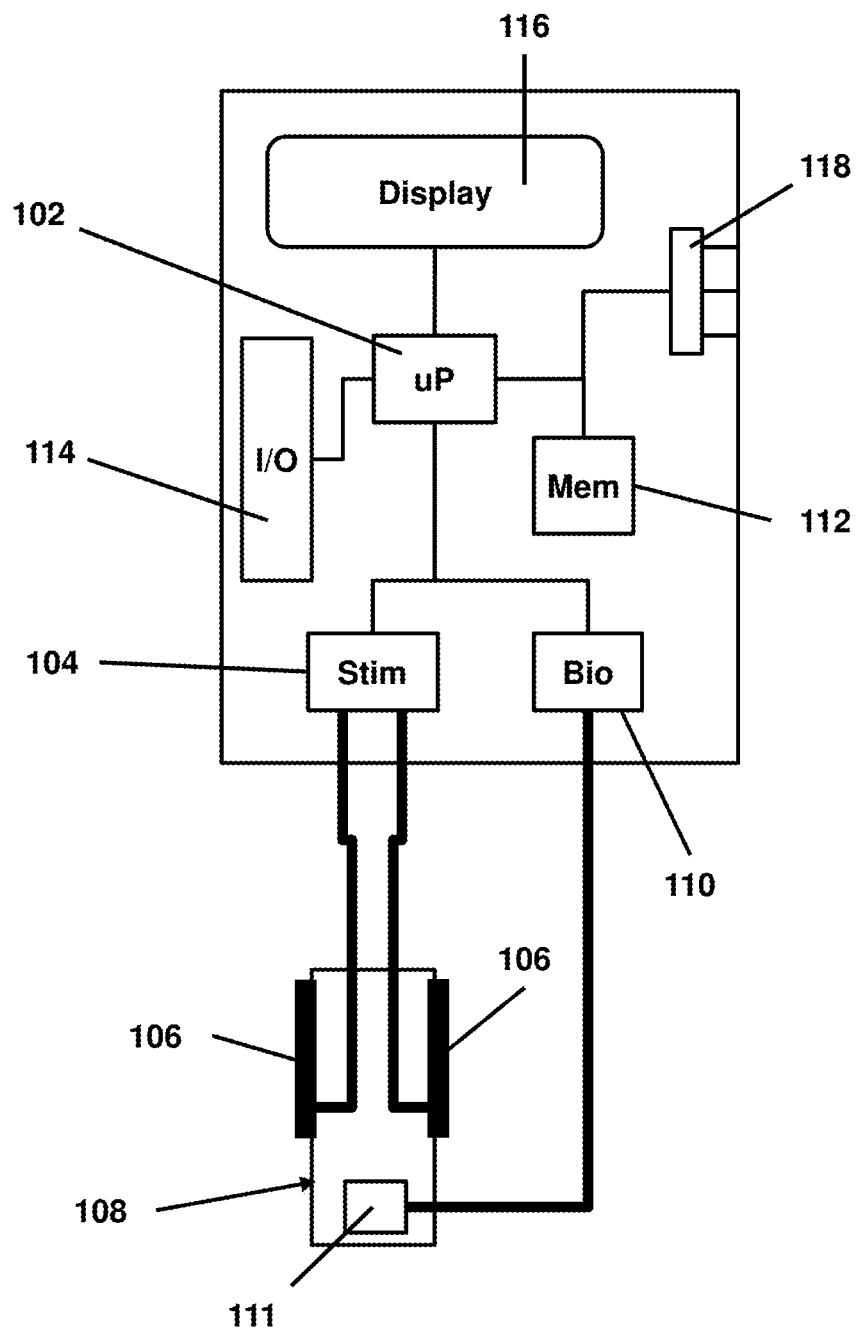
FIG. 1 is a simplified block diagram of an exemplary device.

Referring to FIG. 1, an embodiment of the invention may comprise a processor 102 that is in electronic communication with a stimulator 104. In such an embodiment the stimulator may be in electronic communication with a plurality of electrodes 106. In certain embodiments of the invention, these electrodes may be mounted to a probe device 108 that is configured to position the electrodes correctly when in use. In the illustrated embodiment, the processor 102 may also be in electronic communication with a biofeedback receiver 110. The biofeedback receiver may in turn be in electronic communication with a transducer 111. As shown, the transducer may be incorporated into the probe 108. Other embodiments may provide a transducer as a separate component to be used either in conjunction with the probe or separately when stimulation is not required. In embodiments of the invention, the transducer may be configured to receive electrical signals that are produced by the body when muscles contract. Other embodiments may use various pressure sensors to detect contraction of muscles against the transducer.

As illustrated, the processor 102 may be in electrical communication with a memory 112, an input/output (I/O) section 114 which may comprise such inputs as pushbuttons, sound devices, or other selector devices and input/outputs such as Wi-Fi and other wired or wireless data connections, a display 116, and an external display interface 118. The external display interface may comprise wired and wireless connections to permit embodiments of the invention to communicate to external displays in order to enhance the user's interactions with the device.

Figure 2:
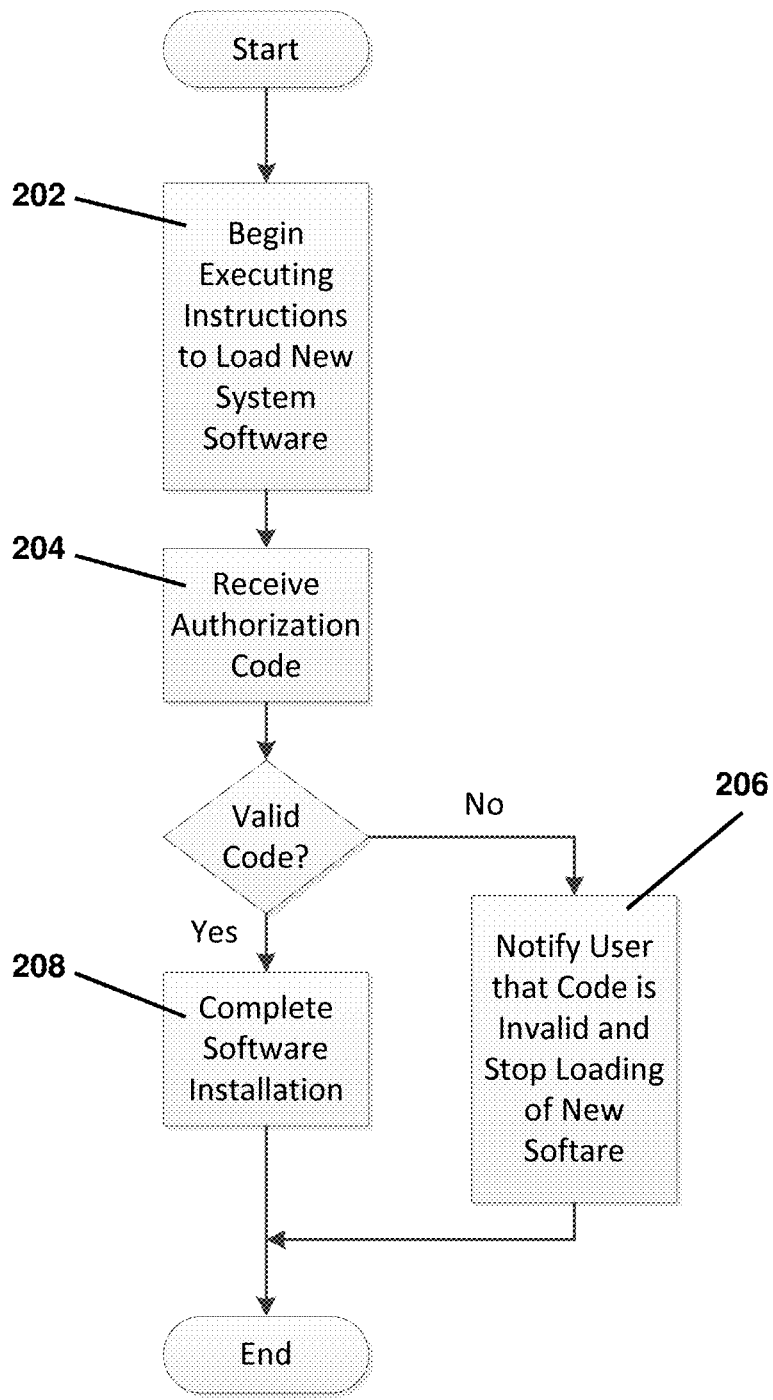
FIG. 2 is a flow chart of exemplary logic for authorizing re-programming of certain functions.

In embodiments of the invention, the memory 112 may be electronically programmable to permit the function of the device to be modified. Such programming may be done with the memory in place via a connection to the I/O section 114 or may be performed externally and written to a memory device that may then be physically inserted into the device such that the memory device is placed in electrical communication with the processor 102. In order to insure device safety, in certain embodiments of the invention, an authorization code may be required to permit reprogramming of the operating software of the device. In an embodiment of the invention, a software update program may be executed by the processor 102 to cause the computer program controlling the operating parameters of the device to be amended. As illustrated in the flowchart of FIG. 2, if the software update program is executed 202, the program instructions may attempt to receive a programming authorization code 204. This receipt may be as the result of a prompt displayed on the display 116 or may be received as part of the process of receiving software instructions uploaded to the device for reprogramming. In order to determine if the programming authorization code is valid, an embodiment of the invention may compare the code to a list of predetermined codes stored in the memory 112 or may execute software instructions which comprise a predetermined code authorization algorithm. For example, an embodiment of the invention may receive a numerical value contained in a collection of software instructions which comprise a software update and apply a predetermined mathematical equation to that numerical value. If the received code does not match the result of the equation, the embodiment of the invention may determine the received code to be invalid. If the received code is invalid the device may notify the user and stop the reprogramming process 206. Alternatively, if the authorization code is valid, the software may begin the reprogramming process 208. As will be described in more detail later herein, embodiments of the invention may comprise interactive games that encourage a user to participate actively in the exercise process (referred to herein as true exercise). The code verification process illustrated in FIG. 2 may also be used to validate the installation of a new or updated interactive game. In such a manner, access to the stimulation portions of the invention may be closely regulated in order to prevent inappropriate or potentially harmful control of the stimulator 104 output section of the invention. Such a method may be used to safeguard a software isolation boundary formed (described in more detail later herein) between the stimulation and biofeedback portions of the invention.

In use, embodiments of the invention may utilize the stimulation section 104 in conjunction with the probe 108 and electrodes 106 to provide a stimulation signal to a user. As the result of the configuration of the probe 108 and control of the stimulation section 104 by the processor 102, a controlled stimulation signal may be output to a user. Such a signal may function to cause a specific set of the user's muscles to contract in a way that provides the necessary stimulation to improve the conditioning of those particular muscles. The level and duration of stimulation may be adjustable in certain embodiments of the invention. One function of the stimulation provided by the invention is to allow a user to experience the contraction sensation that may result in an optimum level of conditioning of a user's pelvic floor muscles. As such, the process of stimulation could be thought of as a process of training the user's muscles to perform a conditioning exercise necessary to further improve the conditioning and resulting performance of the user's muscles. As used in this description, the term "stimulation" has a different meaning than that of "exercise." As used herein, "exercise" or "true exercise" means the voluntary control by a person of certain muscles to provide a desired result whereas, stimulation means that the muscles are stimulated electrically to cause a contraction of the muscle. With regard to pelvic floor muscles, one of the desired results of various combinations of stimulation and exercise is an improvement in a person's ability to control the various muscles regulating the flow of urine.

A user may instruct an embodiment of the invention using an input/output device 114 such as a switch or pushbutton, to start the process of providing a stimulation signal. In embodiments of the invention, a user may be able to select a particular stimulation regimen. For example, a user may select the duration and intensity of the desired stimulation process. Embodiments of the invention may be provided with limitations and warnings to the user in the event that the level and duration of stimulation may exceed a level that is safe or may prove to be uncomfortable to a user.

Figure 3:
FIG. 3 is an exemplary user interface.
Figure 4:
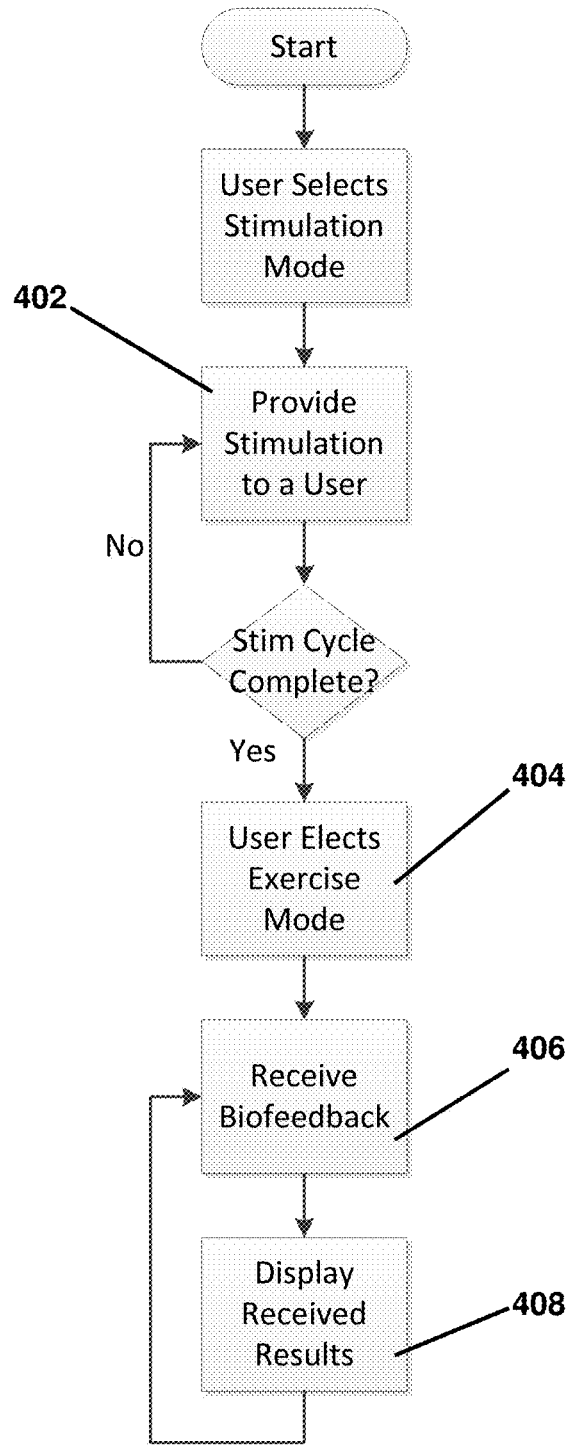
FIG. 4 is a flow chart of exemplary logic for operation of the device.
Figure 5:
FIG. 5 is another exemplary user interface for the device.
Figure 6B:
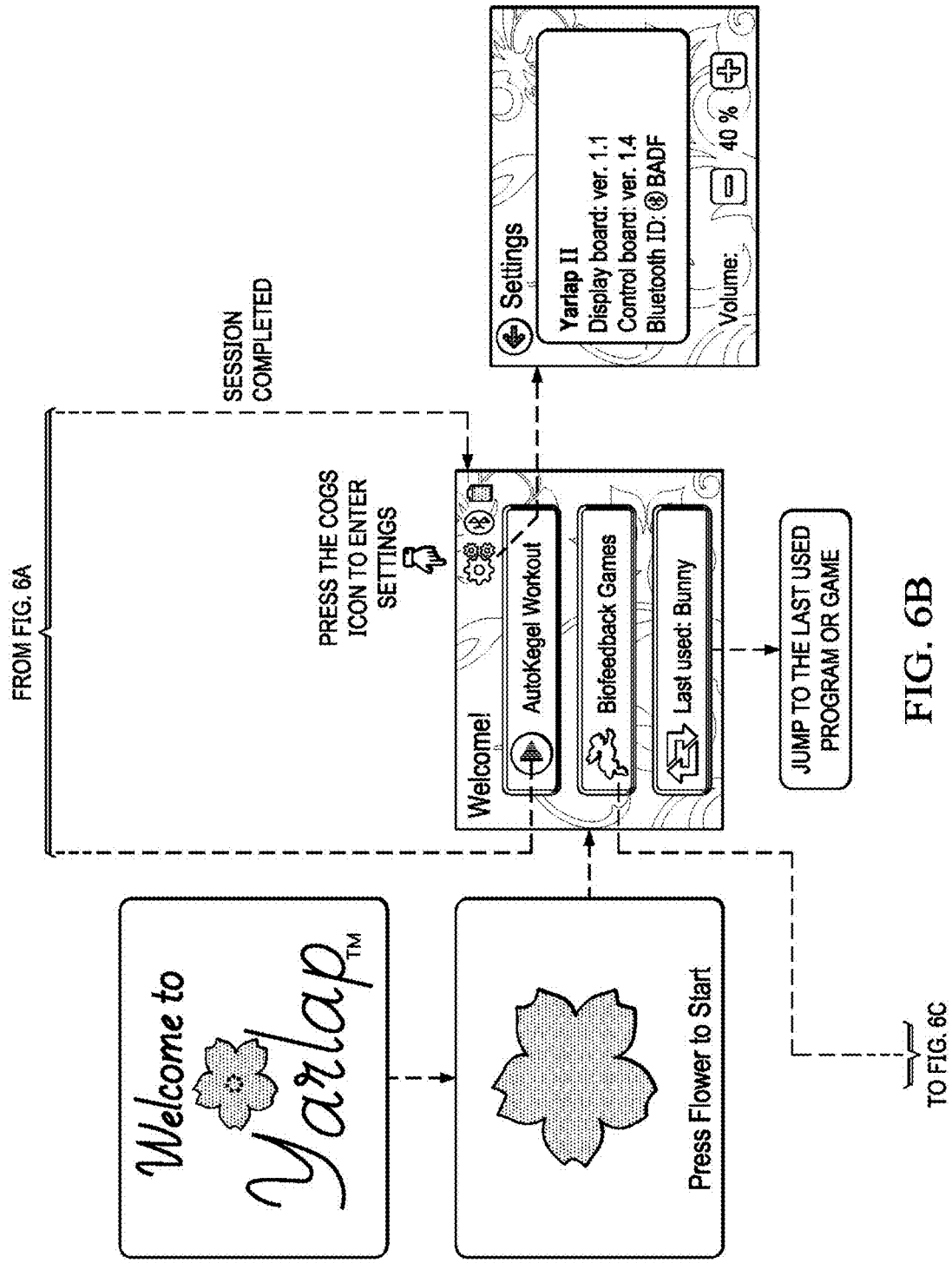
FIG. 6B are additional exemplary user interfaces.
Figure 6C:
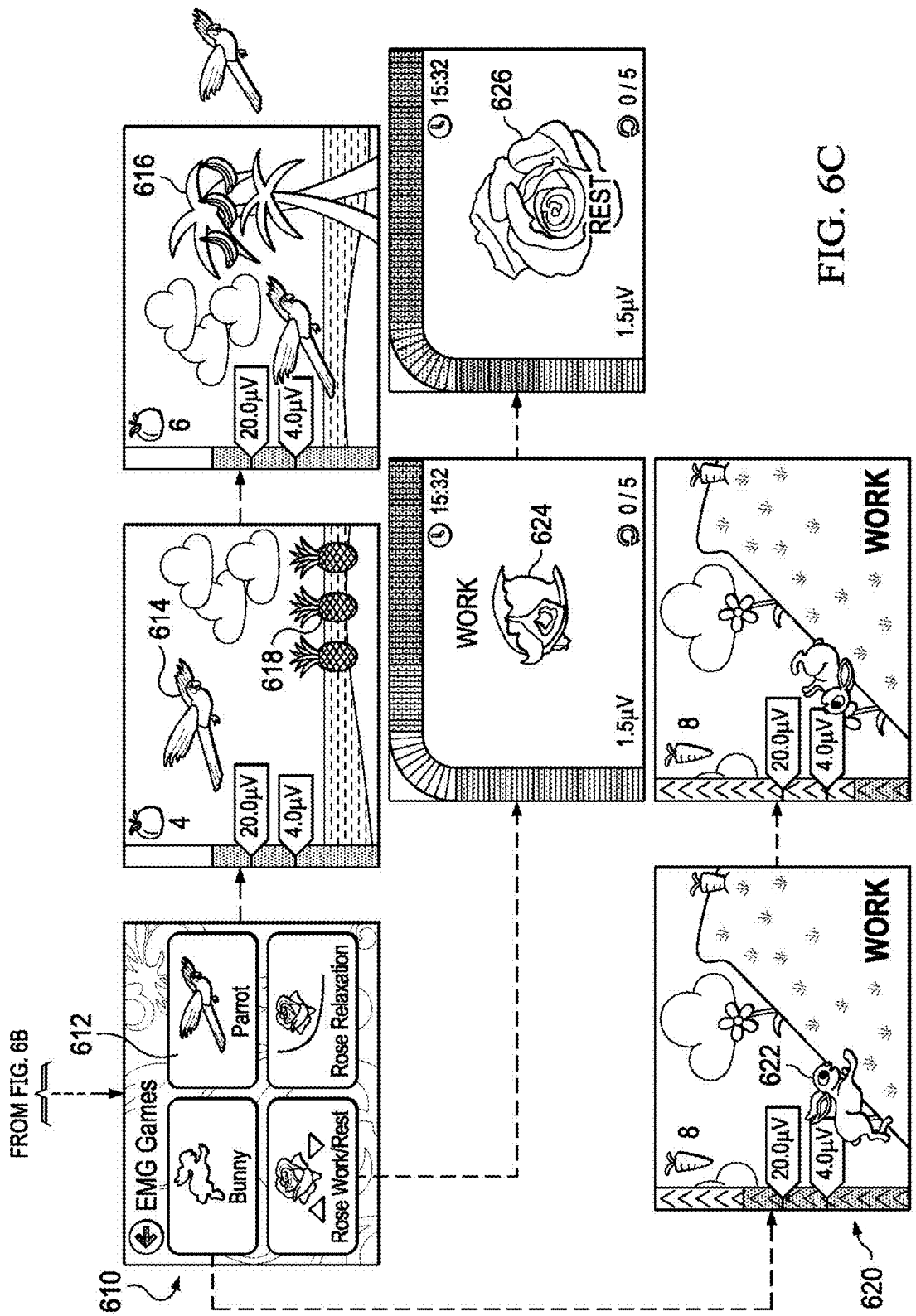
FIG. 6C are additional exemplary user interfaces.

In certain embodiments of the invention, a user may select between a stimulation mode and a biofeedback mode. An example of a user interface presenting such a selection is illustrated in FIG. 3. As is shown, a user may select stimulation 302 or biofeedback 304. As illustrated in the flow chart of FIG. 4, after a user selects stimulation from a menu similar to what is illustrated in FIG. 3, an embodiment of the invention may provide a stimulation signal to a user 402. When in such a mode, a user may be presented with a series of stimulation options. Referring to FIG. 5 which illustrates an example user interface, a user may be presented with menu 502 which provides options for various stimulation characteristics. For example, as illustrated a user may be presented with selections for the treatment of various types of female incontinence. As an example of how an embodiment of the invention may interact with a user, such a user may select a stimulation option from a main menu 300. When a user makes a menu selection, a second level of menu may be displayed 502. As illustrated, an embodiment of the invention may provide the user with additional choices in such a second level menu. Referring to FIG. 6 at 602, a user may select a massage stimulation option. When such an option is selected, a user may be presented with a user interface screen that displays the characteristics of the selected stimulation option 604. A user may elect to start the stimulation program corresponding to the selected option. When started, a user interface may provide feedback to the user in order to properly interact with the stimulation provided by the invention. For example, as illustrated, a user interface may provide an indication of the stimulation provided by the invention 606. In the illustrated example, a user may be required to relax their muscles during portions of the stimulation program. A user interface to provide the necessary feedback to a user is illustrated at 608. As illustrated, the stimulation signal may be removed and a user may be encouraged to relax their muscles to a certain level by a graphical illustration corresponding to a relaxed state. In the example shown, an indicator may be shown that moves across the user interface in response to a biofeedback input received by the invention that corresponds to a measured level of muscle relaxation. In such a manner, an embodiment of the invention may combine a stimulation portion 104 with a biofeedback portion 110.

In embodiments of the invention in which there is an electrical connection between the stimulation and biofeedback portions of the electronic circuitry, allowing the biofeedback portion of the invention to control the stimulation output could potentially result in injury to a user. The capability for such an interaction should be carefully regulated to prevent potentially harmful unauthorized software modifications. In order to provide a level of protection to the user that prevents the stimulation portion of the invention from interacting with the biofeedback portion of the invention, a software "firewall" may be formed to prevent such an interaction. As was described earlier herein, a requirement that software changes require an authorization code in order to be implemented may provide an additional layer of protection in that an unauthorized programmer may be prevented from having the level of access necessary to reprogram the processor 102 to overcome the software firewall. In such a manner, an undesired interaction that could result from unauthorized programming may be prevented.

Figure 7:
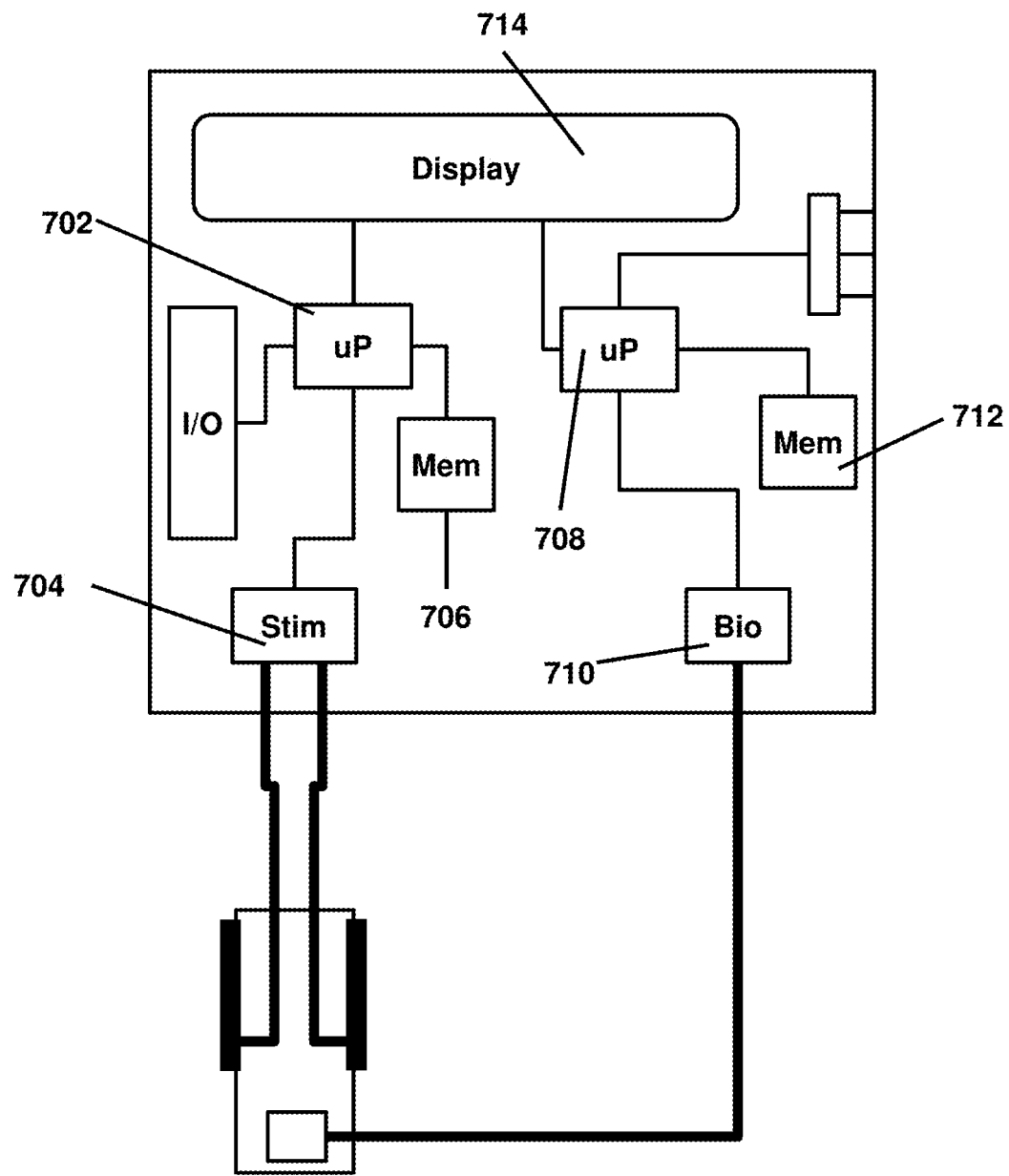
FIG. 7 is a simplified block diagram of another exemplary muscle stimulation device.

In other embodiments of the invention, a physical separation (firewall) between the stimulation portion and the biofeedback portion may be implemented. Such an embodiment is illustrated in FIG. 7. In such an embodiment, a first processor 702 may be in electrical communication with a stimulation portion 704. Software instructions may be contained in a memory 706 that is in electronic communication with the first processor 702. As illustrated, a second processor 708 may be in electronic communication with a biofeedback receiver 710 and a second memory 712. In such a configuration, an embodiment of the invention may have two isolated control sections such that there is a separation between the stimulation and biofeedback portions of the invention. Such a separation may further ensure that there is no undesired interaction between the stimulation and biofeedback portion of the invention. As illustrated, in embodiments of the invention, certain components such as a display portion 714 may be in communication with both the first processor 702 and the second processor 708 while retaining the isolation between the stimulation and biofeedback portions of the invention.

Figure 8:
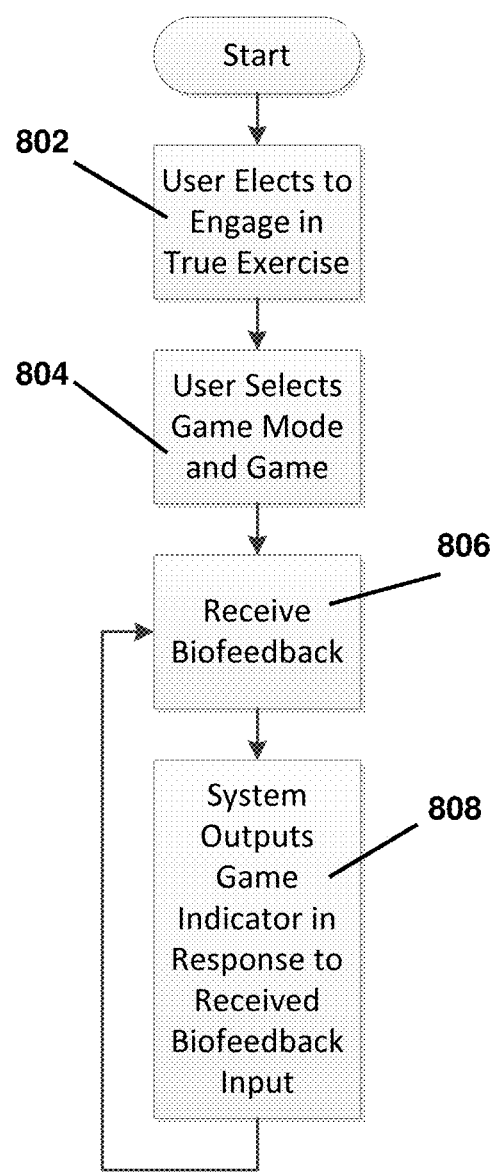
FIG. 8 is a flow chart of an exemplary method for interacting with the device in order to engage in a biofeedback game.

When the user desires to switch from stimulation to true exercise as defined herein, that user may elect to interact solely with the biofeedback portion of the invention. Referring again to the flowchart of FIG. 4, a user may select a biofeedback only operation 404. As illustrated, an embodiment of the invention may then receive biofeedback input data from the biofeedback receiver 110 in step 406. In certain embodiments of the invention, biofeedback results may be displayed to a user 408 in order to guide that user's performance of a series of exercise steps. As shown in the flowchart of FIG. 8, a user may elect to engage in true exercise 802. In step 804, such a user may select an exercise game from one or more such exercise games provided by an embodiment of the invention. During the process of a user's playing such a game, an embodiment of the invention may receive biofeedback data from the biofeedback receiver 102 in step 806. In order to provide feedback to a user, an embodiment of the invention may display a game indicator in response to the received input in step 808.

As with many forms of exercise, keeping the person performing the exercise engaged with the exercise may be facilitated by the use of games or similar competitive tasks. In such methods, providing a user the ability to compete against a series of predetermined tasks or alternatively, against another person, may distract the focus of such a person of the exercise itself and onto the competitive challenge provided by the game. Using such a technique, a user may find it easier and less tedious to perform the desired exercise. In embodiments of the present invention, the exercise goal is to encourage the user to perform a series of muscle contractions and releases of sufficient duration and intensity to produce an improvement in the muscle condition of the pelvic floor muscles of the person performing the exercise. As illustrated in FIG. 6, a user may be presented with a selection of various games 610. In the illustrated embodiment, the selection of games is intended to provide a series of exercise steps directed towards a specific goal. As illustrated, a first game 612 may involve encouraging a user to contract and release their muscles in a specific pattern. In the illustrated example, this is accomplished by displaying a bird 614 that appears to fly through the air. The bird can be made to rise and fall according to the biofeedback received by an embodiment of the invention. In such an embodiment, a rise of the displayed bird 614 may represent a user's increase in the strength of their muscle contraction. Conversely, the bird 614 may fall in response to the user's relaxing their muscles. As the bird 614 appears to fly through the air, a series of obstacles may be presented such that the user must contract their muscles to prevent the bird from colliding with the presented obstacle. Thus, to encourage the user to repeatedly contract their muscles, the series of obstacles 616 (illustrated as trees) may be presented in series according to how long it is desired to require the user to tighten their muscles. Similarly, in order to get the user to relax or vary the strength of the contraction of their muscles, a series of objects or prizes may be displayed 618 (here illustrated as pineapple shapes). Such prizes may be positioned at various levels of the display to encourage a user to maintain a predetermined level of contraction in order to cause the bird shape to pass over the prize.

As illustrated at 620, in other embodiments of the game a user may be encouraged to tighten their muscles to cause a displayed character to rise or fall along an incline as illustrated 622. As shown, the incline may be illustrated as an increasingly steep hill. The user may be encouraged to tighten or relax their muscles to cause the character to move up and down the incline or to hold the character in a certain position. These movements may cause the user to be aware of their ability to partially contract or relax their muscles. Similarly, in another embodiment of such a game, a user may be presented with a shape which can illustrate a contracted or relaxed muscle. As illustrated in FIG. 6 at 624, a flower may be shown as closed when a user's muscles are contracted or open 626 when that same user is causing their muscles to relax.

Figure 9:
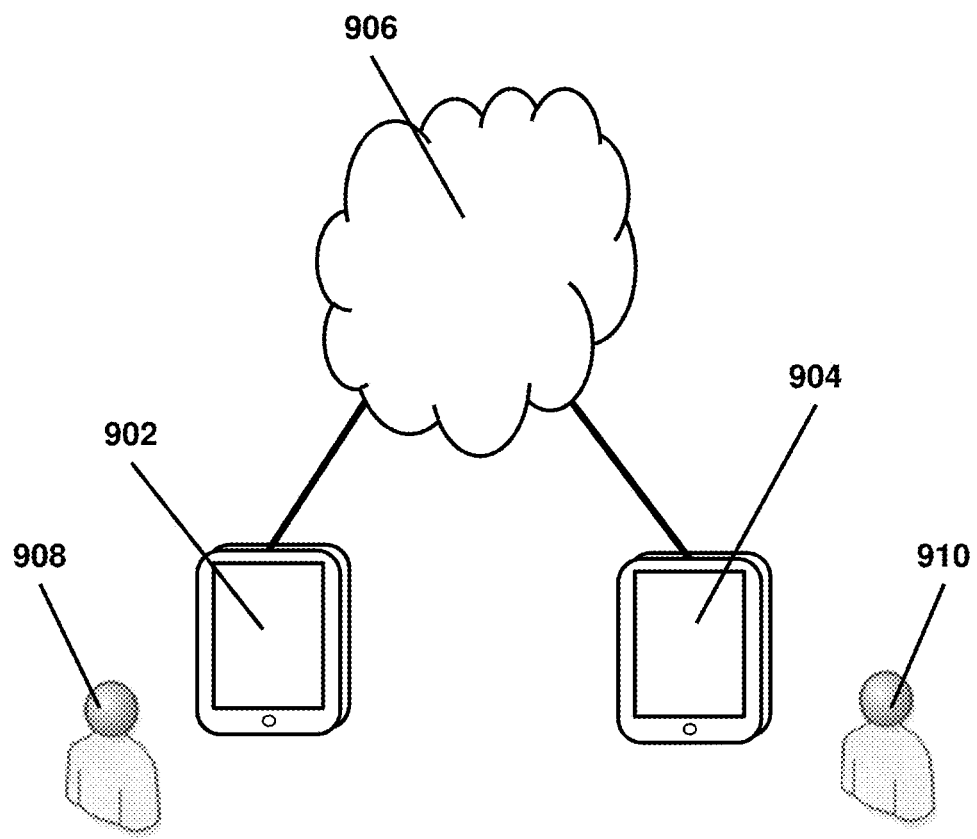
FIG. 9 is a simplified diagram of a system which permits users of devices to compete against each other.

In order to further engage a user, embodiments of the invention may be configured to communicate with other users as illustrated in FIG. 9. As shown, a first device 902 may be placed in electronic communication with a second device 904. As illustrated, the connections are formed using a connection through the internet 906. One ordinarily skilled in the art will understand that the connection from the devices 902 and 904 may involve Wi-Fi, a wired connection, cellular data or other connection methods that may become available. When connected, the user of the first device 908 and the user of the second device 910 may engage in a competitive game play mode in which the first and second user may compete against each other by performing contraction and relaxation movements such that they earn points or progress through a game more quickly than the other player in order to win the competitive game. As with single user game play modes, this embodiment of the invention may serve to further encourage a user to perform conditioning exercises in order to improve their muscle condition to prevent or improve conditions such as incontinence.

Figure 10:
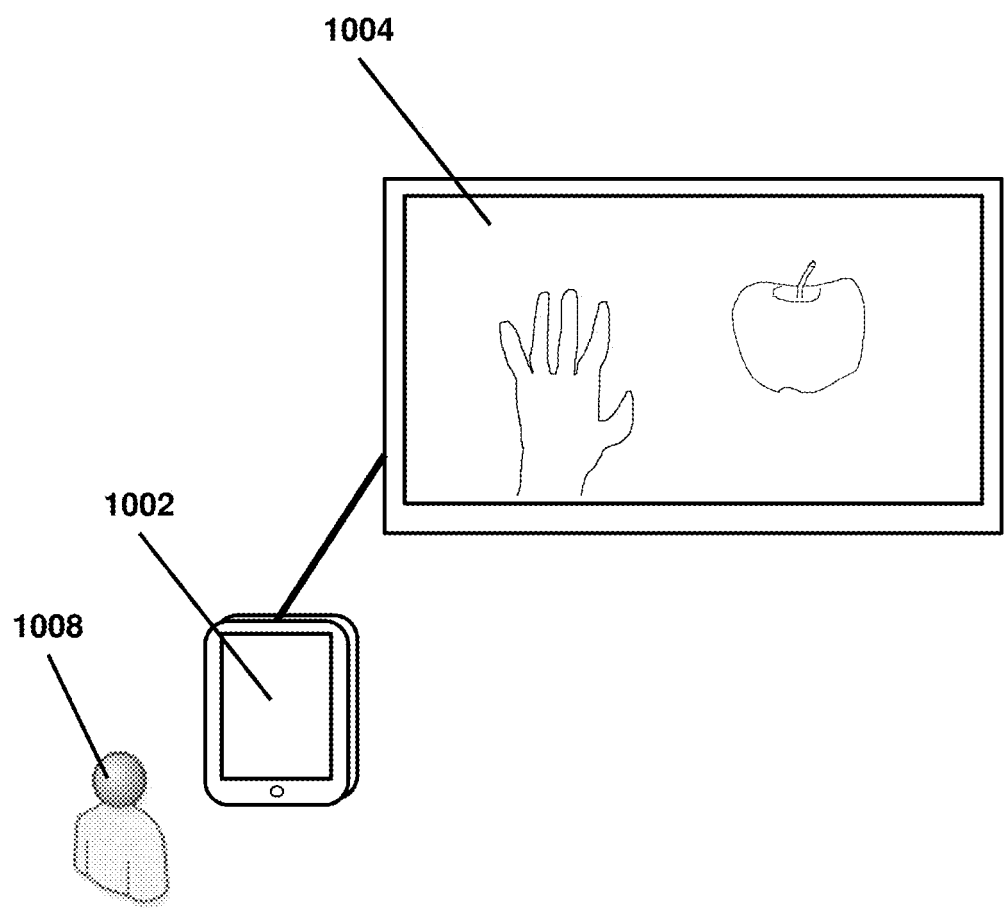
FIG. 10 is a simplified diagram of a visualization tool for the device.
Figure 11:
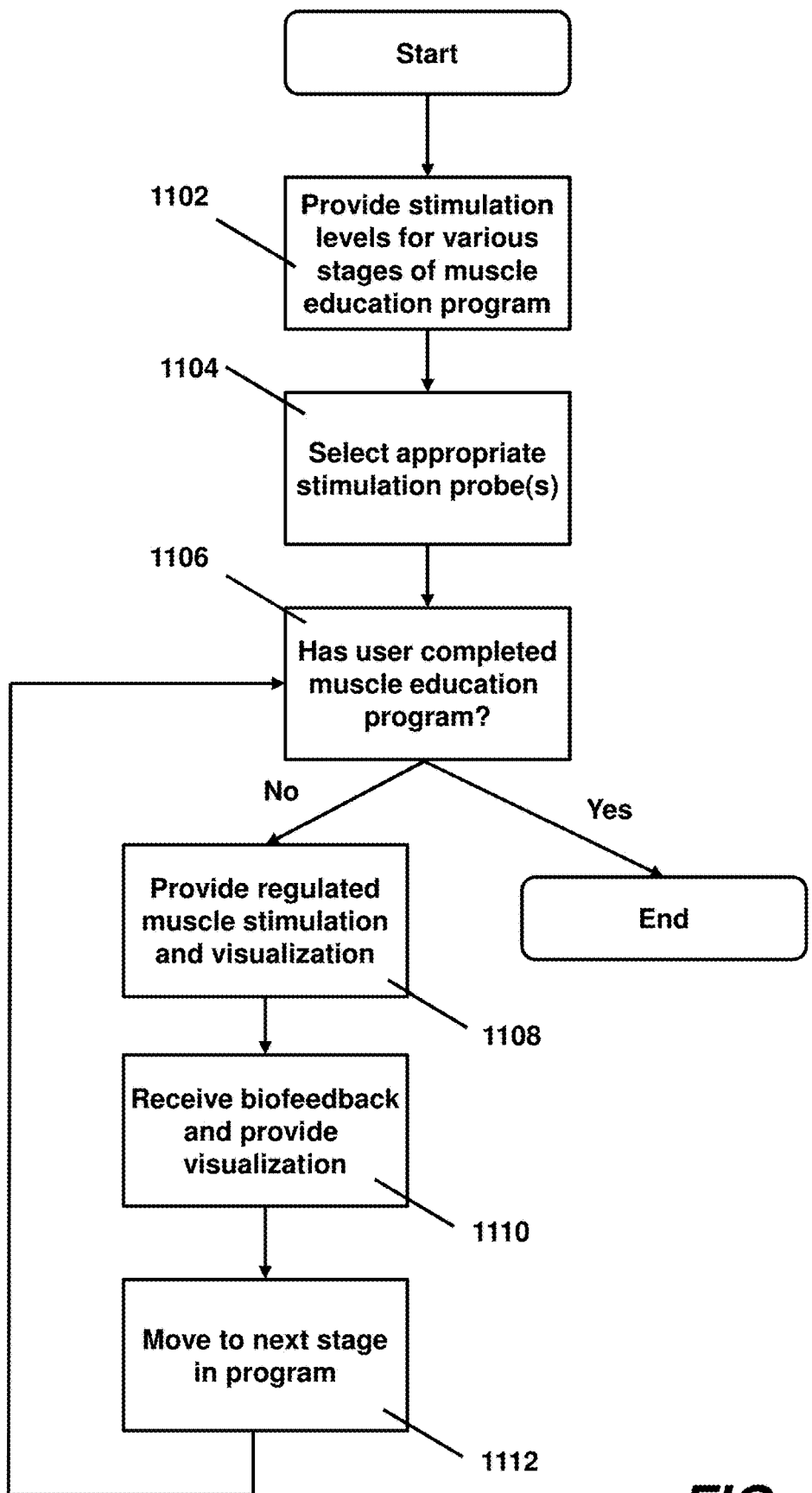
FIG. 11 is a flowchart illustrating exemplary logic for the system of FIG. 10.

FIG. 10 illustrates an exemplary embodiment with a device 1002 in electrical connection with a visualization tool 1004. FIG. 11 illustrates exemplary logic for use with the device 1002 and visualization tool 1004 of FIG. 10. At step 1102, various stimulation levels may be provided for various stages of a muscle education program. Such stimulation levels and stages of the muscle reeducation program may be prescribed, provided in text, chart, or the like. Alternatively, or in addition, such stimulation levels and stages of the muscle reeducation program may be programmed into the device 1002. The muscle stimulation may be selected to reflect a desired outcome. For example, without limitation, the desired outcome may be gripping a hand, moving a finger, extending a leg, standing up, or the like. Too much muscle stimulation may be counter-productive as it may result in regression of muscle education. Too little muscle stimulation may not adequately educate the muscles.

For each individual user the maximum therapeutic efficacy may be achieved, for example without limitation, by way of an algorithmic demonstration of sufficient muscle performance and respiration. Salient to the multi-variable algorithm is the status of the targeted muscle tissues including, but not limited to muscle responsiveness to following the requisite task and a determination of blood flow. Such characteristics may be measured and used to develop a regulated stimulation level specific to the patient and the desired muscle education. If the muscle is unable to perform specific template driven low level contraction challenges and/or exhibits any indications of spasm as monitored by an EMG then the next stimulation (NMES) cycle is blocked and remains arrested for as long as the muscle or muscle group cannot perform the threshold point prequalification parameters. As such, the provided stimulation may be selected based on characteristics of the specific individual user.

Alternatively, or in addition, the provided stimulation may be selected based on the user's condition or injury. In exemplary embodiments, the programmed stimulation levels may be selected to reflect clinical research, best practices, and the like regarding appropriate stimulation levels. Alternatively, or in addition, the device 1002 may be programmed with a number of predetermined stimulation levels associated with various user characteristics and/or injuries or conditions. The user may be prompted with questions to determine the user's characteristics and injury or condition and the device 1002 may suggest or select the associated predetermined stimulation level. Such predetermined stimulation levels may be stored at the memory 704, though such is not required. Regardless, the device 1002 may be regulated to only permit stimulation consistent with the provided stimulation levels for the given stage of the muscle education program.

At step 1104, the device 1002 may be fitted with one or more probes appropriate for the muscle group to be stimulated. For example, without limitation, the probes may be a slender wand, a pad, a sticker, some combination thereof, or the like. The probes may be provided in any number of sizes and shapes.

At step 1106, the device 1002 may determine which stage of the muscle education program the user is at and proceed accordingly. If the program is complete, the session may be ended. Otherwise, at step 1108, the device 1002 may begin with the initial stage and provide regulated muscle stimulation at the device 1002. The device 1002 may simultaneously display a visualization at the visualization tool 1004 at step 1008, though such is not required. The visualization may be of a particular activity and/or the desired outcome. For example, without limitation, the visualization device 1004 may display the image of a hand grasping an apple, a leg kicking a soccer ball, a person standing up, or the like. In this way, the user may associate the stimulation provided with the desired outcome to improve the muscle memory and likelihood that the neural pathways will be educated as desired.

At step 1110, biofeedback may be received at the device 1002. The device 1002 may simultaneously display a visualization at the visualization tool 1004 at step 1110, though such is not required. The visualization may reflect the biofeedback received in view of the desired outcome. For example, without limitation, the visualization device 1004 may display the image of a hand grasping an apple, a leg kicking a soccer ball, a person standing up, or the like consistent with the level of biofeedback received. For example, without limitation, the hand may only be partially contracted, the leg may only be partially extended (or the ball may only travel so far), or the person may only stand up enough to reflect the level of biofeedback received. If the user adequately contracts or relaxes the muscle group, the desired outcome may be displayed. If the user does not adequately contract or relax the muscle group, something less or different from the desired outcome may be displayed. In this way, the user is provided with a visual depiction of their progress towards the desired outcome. Furthermore, the visualization tool may serve as a gamification tool for improving the likelihood that the user will complete the muscle education program. Further still, the user may associate the muscular action with the depicted outcome to improve the muscle memory and likelihood that the neural pathways will be educated as desired. As each stage of the program is completed, at step 1112, the program may be advanced to the next stage.

In some embodiments, the visualization may be provided only with the biofeedback at step 1110. In other embodiments, the visualization may be provided only with the stimulation at step 1108. In still other embodiments, the visualization may be provided with both the stimulation at the feedback at steps 1108 and 1110. In still other embodiments, no visualization may be provided.

The visualization tool 1004 may be one or more electronic displays. The device 1002 and/or the visualization tool 1004 may be configured to display a visualization of the desired outcome. The visualization tool 1004 may be separate from, or integrated with, the device 1002. The visualization tool 1004 may be provided on a phone, tablet, computer, or the like. The visualization tool 1004 may be connected to the device 1002 by way of a wired or wireless connection.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose of specialized computing device. The electronic devices may be personal computers, smartphone, tablets, databases, servers, or the like. The electronic connections described herein may be accomplished by wired or wireless means.

What is claimed is:

1. A system for educating a given muscle group of a user comprising:
    a first processor;
    a first electronic storage device in electronic communication with the first processor;
    a second processor;
    a second electronic storage device in electronic communication with the second processor;
    a biofeedback receiver in electronic communication with the second processor and electrically isolated from the first processor; and a probe configured to be placed in contact with the muscle group comprising:
one or more electrodes positioned on the probe and configured to provide electrical stimulation to the muscle group, wherein the one or more electrodes are in electrical communication with the first processor, are electrically isolated from the second processor, and are electrically isolated from the biofeedback receiver; and
one or more transducers located on the probe and configured to detect contractions of the muscle group, wherein the one or more transducers are in electrical communication with the biofeedback receiver and are not in electronic communication with the on or more electrodes.

2. The system of claim 1 further comprising:
an electronic stimulator configured to produce the electrical stimulation;
a first set of software instructions, stored at the first electronic storage device, which when executed by the first processor, configure the first processor to:
generate, at a display, a prompt requesting user input;
receive user input indicating a selection corresponding to the initiation of a muscle education program; and
in response to the selection, produce, from the electronic stimulator, a series of electrical stimulation signals that are communicated to the one or more electrodes; and
a second set of software instructions, stored at the second electronic storage device, which when executed by the second processor configure the second processor to monitor, at the biofeedback sensor, for signals from the one or more transducers.

3. The system of claim 2 further comprising:
additional software instructions, stored at the second electronic storage device, which when executed by the second processor configure the second processor to cause a first visualization reflecting the signals received from the one or more transducers to be displayed at a visualization device.

4. The system of claim 3 further comprising:
additional software instructions, stored at the first electronic storage device, which when executed by the first processor configure the first processor to cause a second visualization reflecting the signals communicated to the one or more electrodes to be displayed at the visualization device.

5. The system of claim 4 wherein:
the first and second visualizations comprise common imagery depicting a particular movement.

6. The system of claim 5 wherein:
the first and second visualizations are depicted as a game.

7. The system of claim 2 further comprising:
a firewall adapted to prevent the production of the electrical stimulation signals from the first processor while the second set of software instructions are being executed by the second processor to perform biofeedback monitoring.

8. The system of claim 7 wherein:
the firewall comprises software instructions, which are stored at the first electronic storage device.

9. The system of claim 2 further comprising:
a second device;
a network interface in electronic communications with at least the second processor;
additional software instructions, stored at the second electronic storage device, which when executed by the second processor configure the second processor to:
establish an electronic connection to the second device using the network interface;
communicate a signal corresponding to the signal received from the biofeedback receiver to the second device;
receive a signal from the second device corresponding to a biofeedback signal received by the second device; and
display, at a visualization device, an indication of the received signal.

10. The system of claim 2 further comprising:
additional software instructions, stored at the first electronic storage device, which when executed by the first processor configure the first processor to:
generate a prompt at the display requesting a stimulation level to be provided for each stage of a muscle education program;
track which stages have been completed by a user; and
provide, by way of the one or more electrodes, the electrical stimulation to the muscle group, wherein the level and duration of such electrical stimulation is regulated in accordance with the muscle education program.

11. The system of claim 10 wherein:
additional software instructions, stored at the first electronic storage device, which when executed by the first processor, configure the first processor to:
receive an authorization code;
receive program instruction steps;
determine if the authorization code is correct using a predetermined rule; and
cause the first processor to load the program instruction steps into the first electronic device.

12. The system of claim 2 further comprising:
additional software instructions, stored at the first electronic storage device, which when executed by the first processor configure the first processor to:
generate a prompt at the display requesting input of user characteristics and injury;
determine a stimulation level for each stage of a muscle education program associated with the inputted user characteristics and injury;
track which stages have been completed by a user; and
provide, by way of the one or more electrodes, the electrical stimulation to the muscle group, which wherein the level and duration of such electrical stimulation is regulated in accordance with the muscle education program.

\* \* \* \* \*